(12) United States Patent
Wu et al.

(10) Patent No.: US 11,970,391 B2
(45) Date of Patent: Apr. 30, 2024

(54) FLEXIBLE ELECTRODE AND PREPARATION METHOD THEREOF

(71) Applicant: Shenzhen Institutes of Advanced Technology, Guangdong (CN)

(72) Inventors: Tianzhun Wu, Guangdong (CN); Zhaoling Huang, Guangdong (CN); Qi Zeng, Guangdong (CN)

(73) Assignee: Shenzhen Institutes of Advanced Technology, Guangdong (CN)

( * ) Notice: Subject to any disclaimer, the term of this patent is extended or adjusted under 35 U.S.C. 154(b) by 340 days.

(21) Appl. No.: 17/618,198

(22) PCT Filed: Dec. 13, 2019

(86) PCT No.: PCT/CN2019/125389
§ 371 (c)(1),
(2) Date: Dec. 10, 2021

(87) PCT Pub. No.: WO2021/114287
PCT Pub. Date: Jun. 17, 2021

(65) Prior Publication Data
US 2022/0234885 A1 Jul. 28, 2022

(51) Int. Cl.
*B81C 1/00* (2006.01)
*B81B 3/00* (2006.01)

(52) U.S. Cl.
CPC ........ *B81C 1/00166* (2013.01); *B81B 3/0072* (2013.01); *B81B 2201/06* (2013.01);
(Continued)

(58) Field of Classification Search
CPC ......... B81C 1/00166; B81C 2201/0114; B81C 2201/0187; A61B 5/263; A61B 2562/125; A61N 1/04
See application file for complete search history.

(56) References Cited

U.S. PATENT DOCUMENTS

2010/0200538 A1* 8/2010 Petisce ............... B81C 1/00539
216/13
2012/0133247 A1 5/2012 Lee et al.
(Continued)

FOREIGN PATENT DOCUMENTS

CN 106167912 A 11/2016
CN 106646048 A 5/2017
(Continued)

OTHER PUBLICATIONS

CNIPA, International Search Report for International Patent Application No. PCT/CN2019/125389, Sep. 18, 2020, 4 pages.
(Continued)

*Primary Examiner* — Moazzam Hossain
(74) *Attorney, Agent, or Firm* — IP Spring

(57) ABSTRACT

A method for preparing a flexible electrode is provided. The method comprises sequentially forming a flexible base layer and an intermediate conductive layer on a carrier plate; treating an elastomeric template having an electrode pattern with an acid, followed by transferring and printing the electrode pattern onto the intermediate conductive layer to form an electrode inducing layer; forming a titanium dioxide-polydopamine composite layer in a gap of the electrode inducing layer; forming a platinum electrode layer on the titanium dioxide-polydopamine composite layer; removing the carrier plate. The invention solves the problems of slow formation of a polydopamine film and slow formation of a platinum electrode layer. A flexible electrode is further provided.

11 Claims, 5 Drawing Sheets

(52) U.S. Cl.
CPC ... *B81B 2203/0172* (2013.01); *B81B 2203/04* (2013.01); *B81C 2201/0114* (2013.01); *B81C 2201/0185* (2013.01); *B81C 2201/0187* (2013.01); *B81C 2201/0194* (2013.01)

(56) References Cited

U.S. PATENT DOCUMENTS

| | | | |
|---|---|---|---|
| 2017/0086301 A1* | 3/2017 | Minev | H05K 3/28 |
| 2019/0127214 A1 | 5/2019 | Paci et al. | |

FOREIGN PATENT DOCUMENTS

| | | |
|---|---|---|
| CN | 106950267 A | 7/2017 |
| CN | 107123693 A | 9/2017 |
| CN | 107610817 A | 1/2018 |
| CN | 108693225 A | 10/2018 |
| CN | 108751117 A | 11/2018 |
| CN | 109215848 A | 1/2019 |
| CN | 109802013 A | 5/2019 |
| CN | 110314279 A | 10/2019 |

OTHER PUBLICATIONS

Huang, Zhaoling et al., "Fabrication of Implantable Flexible Electrodes Based on Patternable Platium Nanowire and Poly Dopamine Layer," 2019 IEEE 32nd International Conference on Micro Electro Mechanical Systems (MEMS), Oct. 17, 2019, pp. 339-342.
CNIPA, First Office Action for Chinese Patent Application No. 201911286480.1, Dec. 5, 2022, 14 pages.

* cited by examiner

FLEXIBLE ELECTRODE AND PREPARATION METHOD THEREOF

CROSS-REFERENCE TO RELATED APPLICATION

This application is the U.S. National Stage filing under 35 U.S.C. § 371 of International Patent Application No. PCT/CN2019/125389, filed on Dec. 13, 2019.

FIELD OF THE INVENTION

The invention relates to the technical field of preparation of flexible electrode, in particular to a flexible electrode and a preparation method thereof.

BACKGROUND OF THE INVENTION

The current flexible electrode manufactured based on traditional MEMS (Micro-Electro-Mechanical System) technology mainly includes a flexible base layer and a metal electrode layer disposed thereon. However, Young's modulus of the surface metal layer does not match well with that of the flexible base layer, which is likely to cause the metal layer to peel off. Based on this, studies have shown that a polydopamine film provides a solution to the mismatch between the Young's modulus of the metal layer and that of the flexible base layer, and enhances the adhesion between them.

Usually, a polydopamine film is formed by self-assembly of its precursor solution (such as a mixture of dopamine hydrochloride and a Tris buffer solution), but the self-assembling process takes a long time, usually more than 24 hours. The use of strong oxidants or ultraviolet light can increase the speed of forming a film from polydopamine to a certain extent. Nevertheless, strong oxidants are highly toxic to medical devices, and the use of ultraviolet light alone, even if it is environmentally friendly, will not greatly increase the speed of forming a film from polydopamine (usually 30 nm/6 h).

In addition, for medical flexible electrodes, it is necessary to deposit platinum, a metal with good biocompatibility, on the polydopamine film. However, due to the high work function of platinum, it takes more than 72 hours to deposit platinum ions on the polydopamine film to form a platinum metal layer, resulting in a long process of preparing a flexible electrode.

Therefore, it is necessary to provide an environmentally friendly method for rapidly preparing a flexible electrode.

SUMMARY OF THE INVENTION

A method for preparing a flexible electrode is provided herein. The method allows nano-titanium dioxide and polydopamine precursor solution to be subject to electrophoresis under ultraviolet light, thereby greatly increasing the speed of forming a film from polydopamine and then the speed of reducing platinum ions to the platinum electrode layer. The method solves the problems that the polydopamine is difficult to form a film quickly, and the platinum electrode layer is difficult to form quickly.

In a first aspect, the present invention provides a method for preparing a flexible electrode, comprising:
providing a carrier plate, and sequentially forming a flexible base layer and an intermediate conductive layer on a side of the carrier plate;
preparing an elastomeric template with an electrode pattern, and treating the elastomeric template with an acid, followed by transferring and printing the electrode pattern of the elastomeric template onto a surface of the intermediate conductive layer by microcontact printing such that an electrode inducing layer complementary to the electrode pattern is formed on the intermediate conductive layer;
adding a mixture of nano titanium dioxide and a solution of polydopamine precursor onto the intermediate conductive layer that is not covered by the electrode inducing layer, using a glass with a transparent conductive layer as a cathode, and the intermediate conductive layer as an anode, disposing the transparent conductive layer and the intermediate conductive layer opposite to each other, forming a titanium dioxide-polydopamine composite layer in a gap of the electrode inducing layer by electroplating and oxidizing the anode under ultraviolet light;
adding a solution of platinum ion onto surfaces of the titanium dioxide-polydopamine composite layer and the electrode inducing layer, using a glass with a transparent conductive layer as an anode, and the intermediate conductive layer as a cathode, disposing the transparent conductive layer facing to the intermediate conductive layer, forming a platinum electrode layer on the titanium dioxide-polydopamine composite layer by reducing the cathode under ultraviolet light;
removing the carrier plate to obtain the flexible electrode.

In one embodiment, the elastomeric template with an electrode pattern is prepared by steps of
applying a photoresist on a hard substrate by spin coating, and performing exposure with a mask having a specific shape and developing to obtain a positive film with the electrode pattern; and
casting a molding adhesive onto the positive film, which is removed after curing to obtain the elastomeric template with the electrode pattern.

In one embodiment, the acid comprises at least one of hydrofluoric acid, nitric acid and hydrochloric acid. Treating the elastomeric template with acid facilitates the formation of the electrode inducing layer complementary to the electrode pattern on the intermediate conductive layer.

In one embodiment, a pressure of 1.0-2.0 N is applied during the microcontact printing.

In one embodiment, the solution of polydopamine precursor is a solution of dopamine hydrochloride in Tris, and the solution of polydopamine precursor has a pH of 6-9 and a concentration of dopamine hydrochloride of 2-5 mg/mL.

In one embodiment, a concentration of nano-titanium dioxide ($TiO_2$) in the mixture is in a range of 0.05-0.25 mg/mL.

Optionally, in the mixture, the mass ratio of nano-titanium dioxide to dopamine hydrochloride is in a range of (0.025-0.05):1.

In one embodiment, a DC voltage of 1-5V is applied between the cathode and the anode in the processes of oxidizing the anode and reducing the cathode.

In one embodiment, the ultraviolet light has an energy density of 0.7-5 $mW/cm^2$ in the processes of oxidizing the anode and reducing the cathode.

In one embodiment, a distance between the cathode and the anode is in a range of 1-5 mm in the processes of oxidizing the anode and reducing the cathode.

In one embodiment, in the process of forming the titanium dioxide-polydopamine composite layer, the ultraviolet light is applied for 3-15 minutes, and the voltage is applied between the cathode and the anode for 3-15 minutes.

Optionally, in the process of forming the platinum electrode layer, the ultraviolet light is applied for 20-120 minutes, and the voltage is applied between the cathode and the anode for 20-120 minutes.

The method for preparing a flexible electrode provided in the first aspect of the present invention has the following advantages. 1. The method greatly improves the speed of oxidizing and forming a film from dopamine and then permits rapid formation of a titanium dioxide-polydopamine composite layer, by a combination of electrophoresis deposition technology with ultraviolet light which causes electron transitions within nano-$TiO_2$ and increases the amount of active oxygen in the mixture of $TiO_2$ and polydopamine precursor solution. 2. A combination of electrophoresis deposition technology with ultraviolet light allows to control the amount of hydroxyl group in the platinum ion solution by nano-titanium dioxide. With the help of the active groups of polydopamine and the reduction of nano-$TiO_2$ in the titanium dioxide-polydopamine composite layer under ultraviolet light, the speed of reducing platinum ion to platinum electrode layer greatly increases. Thus, the method is especially suitable for the production of large-area electrode layers. 3. The titanium dioxide-polydopamine composite layer has a certain adhesion, and is possible to form chemical bonds with the platinum electrode layer and the intermediate conductive layer through its various molecular bonds so as to improve the adhesion between them, thereby enhancing the bonding between the platinum electrode layer and the flexible base layer to a certain extent. 4. An electrode inducing layer complementary to the electrode pattern can be quickly formed on the intermediate conductive layer by transferring and printing, and the elastomeric template with the electrode pattern can be used repeatedly.

In short, the preparation method is simple and easy without the use of expensive equipment and toxic reagents. The deposition technique used herein, i.e., electrophoresis deposition under light, greatly improves the efficiency of forming the titanium dioxide-polydopamine composite layer and the platinum electrode layer, and is environmentally friendly and efficient, thereby reducing the manufacturing cost of flexible electrodes.

In a second aspect, the present invention provides a flexible electrode, comprising:

a flexible base layer, and an intermediate conductive layer and an electrode inducing layer sequentially arranged on a surface of the flexible base layer, wherein a titanium dioxide-polydopamine composite layer is arranged in a gap of the electrode inducing layer, and a platinum electrode layer is arranged on the titanium dioxide-polydopamine composite layer. The flexible electrode can be prepared by the method described in the first aspect of the present invention.

In one embodiment, the polydopamine is chelated with platinum atoms at the interface between the titanium dioxide-polydopamine composite layer and the platinum electrode layer.

In one embodiment, material of the electrode inducing layer is an insulating material, specifically the residual material remaining after the reaction between the molding adhesive and the acid.

In one embodiment, the flexible base layer has a thickness of 2-6 μm.

In one embodiment, the intermediate conductive layer has a thickness of 10-30 nm.

In one embodiment, the titanium dioxide-polydopamine composite layer has a thickness of 80-500 nm.

In one embodiment, the platinum electrode layer has a thickness of 0.3-5 μm.

In the flexible electrode provided in the second aspect of the present invention, the flexible base layer and the platinum electrode layer are connected through an intermediate conductive layer and an adhesive titanium dioxide-polydopamine composite layer. The titanium dioxide-polydopamine composite layer forms chemical bonds with the platinum electrode layer and the intermediate conductive layer through its various molecular bonds so as to improve the adhesion between them with the help of non-covalent bonds, thereby enhancing the bonding between the platinum electrode layer and the flexible base layer to a certain extent. The resulting patterned platinum electrode layer has a small electrical impedance, which improves its safety in biological applications.

The advantages of the present invention will be partially explained below, and part of the advantages are apparent from the description, or can be learned through the implementation of the embodiments of the present invention.

DETAILED DESCRIPTION OF ILLUSTRATED EMBODIMENTS

Figure 1:
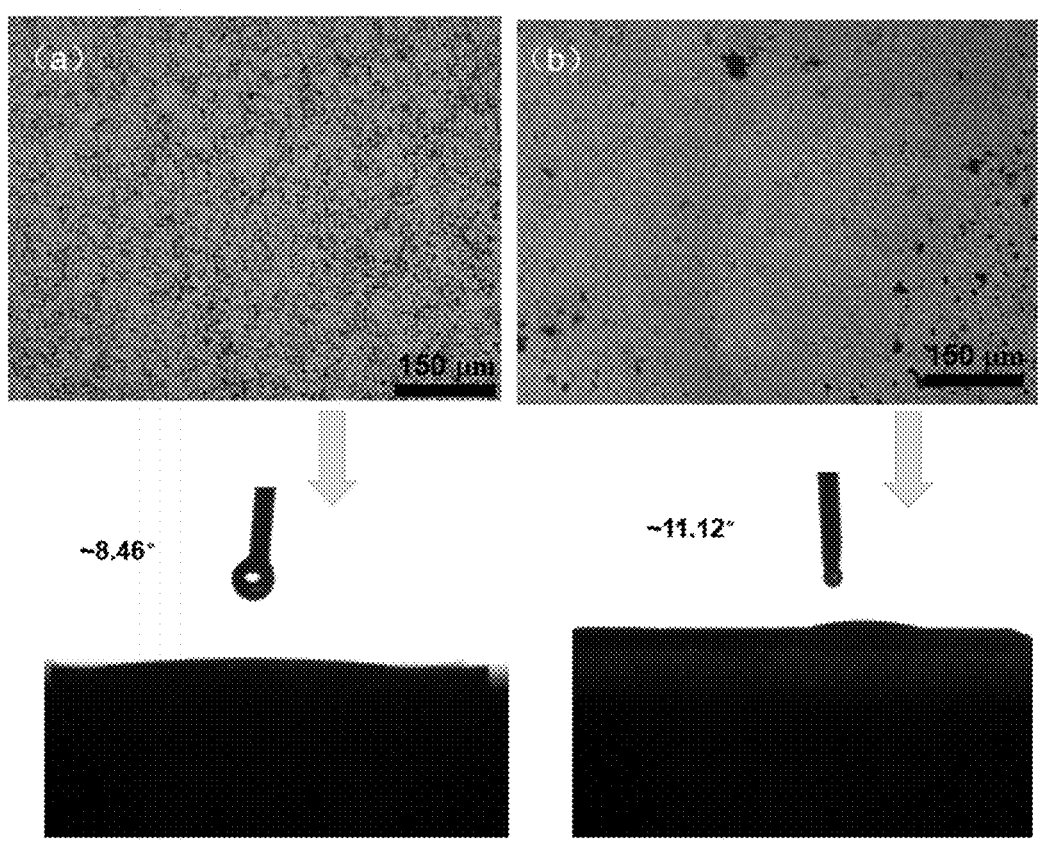
FIG. 1 shows the morphology of the polydopamine film and the corresponding contact angle formed (a) in the presence of nano-$TiO_2$ and (b) in the absence of nano-$TiO_2$.

The following describes preferred embodiments of the present invention. It should be noted that those skilled in the art can make several improvements or modifications without departing from the principles of the embodiments of the present invention. These improvements or modification are also considered as the protection scope of the present invention.

A method for preparing a flexible electrode according one embodiment of the present invention comprises the following steps:

provided a carrier plate, and sequentially forming a flexible base layer and an intermediate conductive layer on a side of the carrier plate;

preparing an elastomeric template with an electrode pattern, and treating the elastomeric template with an acid, followed by transferring and printing the electrode pattern of the elastomeric template onto a surface of the intermediate conductive layer by microcontact printing such that an electrode inducing layer complementary to the electrode pattern is formed on the intermediate conductive layer;

adding a mixture of nano titanium dioxide and a solution of polydopamine precursor onto the intermediate conductive layer that is not covered by the electrode inducing layer, using a glass with a transparent conductive layer as a cathode, and the intermediate conductive layer as an anode, disposing the transparent conductive layer and the intermediate conductive layer opposite to each other, forming a titanium dioxide-polydopamine composite layer in a gap of the electrode inducing layer by electroplating and oxidizing the anode under ultraviolet light;

adding a solution of platinum ion onto surfaces of the titanium dioxide-polydopamine composite layer and the electrode inducing layer, using a glass with a transparent conductive layer as an anode, and the intermediate conductive layer as a cathode, disposing the transparent conductive layer facing to the intermediate conductive layer, forming a platinum electrode layer on the titanium dioxide-polydopamine composite layer by reducing the cathode under ultraviolet light;

removing the carrier plate to obtain the flexible electrode.

The material of the carrier plate herein comprises glass, silicon, plastic, metal or ceramic. The carrier plate is mainly used as the foundation for the subsequent layers, and should be removed after each layer is completed.

The flexible base layer herein may be formed by coating. The material of the flexible base layer is a flexible insulating material selected from a group consisting of polyimide (PI), polyethylene terephthalate (PET), polyethylene naphthalate (PEN), polymethyl methacrylate (PMMA) and polyurethane (PUA). The flexible base layer is preferably polyimide, which has good bending resistance and insulation properties.

The material of the intermediate conductive layer herein comprises but not limited to one or more of titanium, gold, silver, copper, palladium, niobium, tantalum and their alloys, titanium nitride (TixNy), iridium oxide (IrOx), indium tin oxide (ITO), aluminum-doped zinc oxide (AZO), fluorine-doped tin dioxide (FTO) and phosphorus-doped tin dioxide (PTO).

Optionally, the intermediate conductive layer can be formed by the processes of magnetron sputtering, chemical vapor deposition, electron beam evaporation, pulsed laser deposition, resistance evaporation, or spin coating.

Optionally, the flexible base layer has a thickness of 2-6 μm.

Optionally, the intermediate conductive layer has a thickness of 10-30 nm. The intermediate conductive layer is relatively thin, and it mainly plays a role of electrical conductor in the subsequent processes of oxidizing the anode and reducing the cathode.

The elastomeric template with an electrode pattern is prepared by steps of applying a photoresist on a hard substrate by spin coating, and performing exposure with a mask having a specific shape and developing to obtain a positive film with the electrode pattern; and casting a molding adhesive onto the positive film, which is removed after curing to obtain the elastomeric template with the electrode pattern. The elastomeric template has an electrode pattern complementary to the positive film. Apparently, the elastomeric template is made of the same material as the molding adhesive.

The material of the elastomeric template is selected from one or more of polydimethylsiloxane, polyethylene glycol diacrylate, polymethyl methacrylate, ethylene-vinyl acetate copolymer, polyurethane and silica gel, but not limited to these.

Optionally, the molding adhesive may be polydimethylsiloxane (PDMS). The PDMS herein may comprise glue A and glue B in a volume ratio of 1:10. In other embodiment, the molding adhesive may be one of polyethylene glycol diacrylate (PEGDA), polymethyl methacrylate (PMMA), ethylene-vinyl acetate copolymer (EVA), polyurethane (PUA) and silica gel, but not limited to these. Any other molding adhesive suitable for soft lithography is possible.

The acid used in the acid treatment comprises at least one of hydrofluoric acid, nitric acid and hydrochloric acid. Treating the elastomeric template with acid facilitates the formation of the electrode inducing layer complementary to the electrode pattern on the intermediate conductive layer. The shape of the electrode inducing layer is the same as the shape of the elastomeric template. Optionally, the acid is a mixture of hydrochloric acid and nitric acid with a volume ratio of 3:1, or a mixture of hydrofluoric acid and nitric acid with a volume ratio of 3:1.

A pressure of 1.0-2.0 N is applied during the microcontact printing. This ensures the polydopamine adhesion layer with the electrode pattern is completely transferred and printed to the surface of the thinner intermediate conductive layer, and ensures no deformation of the carrier plate (for example, silicon wafer, glass substrate, etc.) occurs and no internal stress generates under such pressure.

The solution of polydopamine precursor is a solution of dopamine hydrochloride in Tris, and the solution of polydopamine precursor has a pH of 6-9 and a concentration of dopamine hydrochloride of 2-5 mg/mL.

A concentration of nano-titanium dioxide ($TiO_2$) in the mixture is in a range of 0.05-0.25 mg/mL.

Optionally, in the mixture, the mass ratio of nano-titanium dioxide to dopamine hydrochloride is in a range of (0.025-0.05):1.

The material of the transparent conductive layer herein comprises but not limited to at least one of indium tin oxide (ITO), aluminum-doped zinc oxide (AZO), fluorine-doped tin dioxide (FTO), phosphorus-doped tin dioxide (PTO), titanium nitride (TixNy) and iridium oxide (IrOx).

Optionally, the titanium dioxide-polydopamine composite layer has a thickness of 80-500 nm. Such thickness can be adjusted by adjusting the durations of applying ultraviolet light and voltage between the anode and cathode. If there is a current between the cathode and anode, the droplets of the mixture of nano-$TiO_2$ and polydopamine precursor solution will quickly fill the gap of the electrode inducing layer due to the electrophoresis. Furthermore, under the ultraviolet light, oxygen free radicals produced by $TiO_2$ and ultraviolet light together promote the rapid oxidation of polydopamine precursors to form polydopamine, and then the formation of a titanium dioxide-polydopamine composite layer.

Optionally, in the process of oxidizing the anode, a DC voltage of 1-5V is applied between the cathode and the anode. The voltage is applied for 3-15 min.

Optionally, in the process of forming the titanium dioxide-polydopamine composite layer, the ultraviolet light has an energy density of 0.7-5 mW/cm$^2$ and a wavelength of 350-380 nm. Optionally, in the process of forming the titanium dioxide-polydopamine composite layer, the ultraviolet light is applied for 3-15 minutes. The duration of applying ultraviolet light can be equal to or different from the duration of applying voltage.

In the process of oxidizing the anode, a distance between the cathode and the anode is in a range of 1-5 mm. A larger distance will cause a great loss of ultraviolet light reaching the electrode inducing layer, and a small density of the cell line between the cathode and the anode.

In one embodiment of the present invention, the ultraviolet light reaches on a surface of the cathode away from the transparent conductive layer in the process of oxidizing the anode. Because the whole cathode is transparent, ultraviolet light can pass through the cathode so as to reach the electrode inducing layer. In other embodiments of the present invention, the ultraviolet light can also reach a surface of the cathode away from the transparent conductive layer and a surface of the carrier plate away from the flexible base layer at the same time. That is, the ultraviolet light is applied to the upper and lower ends of the cathode and the anode that are arranged oppositely.

Optionally, the platinum electrode layer has a thickness of 0.3-5 μm. Such thickness can be adjusted by adjusting the durations of applying ultraviolet light and voltage between the anode and cathode.

Electrophoresis causes electrowetting on the surface interface, in the present of a current. As a result, the titanium dioxide-polydopamine composite layer and the electrode inducing layer get wet due to the flow of the droplets of the platinum ion solution passing through. With the droplets passing through the titanium dioxide-polydopamine composite layer, the charges generated by irradiating the semiconductor material such as titanium dioxide with ultraviolet light, and the large number of phenolic hydroxyl and amine groups of polydopamine together promote the faster reduction of platinum metal ions, such that a patterned platinum electrode layer is formed on the titanium dioxide-polydopamine composite layer.

Optionally, in the process of reducing the cathode, a DC voltage of 1-5V is applied between the cathode and the anode. Optionally, the voltage is applied for 20-120 min.

Optionally, in the process of forming the platinum electrode layer, the ultraviolet light has an energy density of 0.7-5 mW/cm$^2$ and a wavelength of 350-380 nm. Optionally, in the process of forming the platinum electrode layer, the ultraviolet light is applied for 20-120 minutes. The duration of applying ultraviolet light can be equal to or different from the duration of applying voltage.

In the process of reducing the cathode, a distance between the cathode and the anode is in a range of 1-5 mm. A larger distance will cause a great loss of ultraviolet light reaching the electrode inducing layer and the titanium dioxide-polydopamine composite layer, and a small density of the cell line between the cathode and the anode.

In one embodiment of the present invention, the ultraviolet light reaches on a surface of the cathode away from the transparent conductive layer in the process of reducing the cathode. Because the whole cathode is transparent, ultraviolet light can pass through the cathode so as to reach the titanium dioxide-polydopamine composite layer. In other embodiments of the present invention, the ultraviolet light can also reach a surface of the cathode away from the transparent conductive layer and a surface of the carrier plate away from the flexible base layer at the same time in the process of reducing the cathode. That is, the ultraviolet light is applied to the upper and lower ends of the cathode and the anode that are arranged oppositely.

The platinum electrode layer herein comprises a plurality of stimulation electrode sites and a plurality of electrode connection points opposite to each other, and each of the stimulation electrode sites connects to each of the electrode connection points by a wire.

One embodiment further comprises the following steps prior to the step of removing the carrier plate: preparing a sealing layer on the platinum electrode layer and the electrode inducing layer such that the stimulation electrode sites and the electrode connection points of the platinum electrode layer are exposed from the sealing layer.

The material of the sealing layer may be the same as or different from the material of the flexible base layer. Optionally, the material of the sealing layer is independently selected from one or more of polyimide, PDMS, silica gel, epoxy resin, polystyrene and polybutylene terephthalate (PET). The sealing layer is provided for the purpose of protecting the platinum electrode layer without affecting its use.

The sealing layer can be formed by injection molding, die casting or photolithography. In one embodiment of the present invention, the sealing layer is prepared as follows:

b1, disposing a sealing film on the platinum electrode layer, the sealing film further covers a part of the electrode inducing layer that is not covered by the platinum electrode layer;

b2, coating a sacrificial material on the sealing film, and etching a sacrificial layer formed thereon to form a patterned sacrificial layer;

b3, dry-etching the sealing film using the patterned sacrificial layer as a mask so as to expose the platinum electrode layer;

b4, removing the sacrificial layer to form the sealing layer.

The method for preparing a flexible electrode provided in the first aspect of the present invention has the following advantages. 1. The method greatly improves the speed of oxidizing and forming a film from dopamine and then permits rapid formation of a titanium dioxide-polydopamine composite layer, by a combination of electrophoresis deposition technology with ultraviolet light which causes electron transitions within nano-TiO$_2$ and increases the amount of active oxygen in the mixture of TiO$_2$ and polydopamine precursor solution. 2. A combination of electrophoresis deposition technology with ultraviolet light allows to control the amount of hydroxyl group in the platinum ion solution by nano-titanium dioxide. With the help of the active groups of polydopamine and the reduction of nano-TiO$_2$ in the titanium dioxide-polydopamine composite layer under ultraviolet light, the speed of reducing platinum ion to platinum electrode layer greatly increases. Thus, the method is especially suitable for the production of large-area electrode layers. 3. The titanium dioxide-polydopamine composite layer has a certain adhesion, and is possible to form chemical bonds with the platinum electrode layer and the intermediate conductive layer through its various molecular bonds so as to improve the adhesion between them, thereby enhancing the bonding between the platinum electrode layer and the flexible base layer to a certain extent. 4. An electrode inducing layer complementary to the electrode pattern can be quickly formed on the intermediate conductive layer by transferring and printing, and the elastomeric template with the electrode pattern can be used repeatedly.

In short, the preparation method is simple and easy without the use of expensive equipment and toxic reagents. The deposition technique used herein, i.e., electrophoresis deposition under light, greatly improves the efficiency of forming the titanium dioxide-polydopamine composite layer and the platinum electrode layer, and is environmentally friendly and efficient, thereby reducing the manufacturing cost of flexible electrodes.

A flexible electrode according one embodiment of the present invention comprises:

a flexible base layer, and an intermediate conductive layer and an electrode inducing layer sequentially arranged on a surface of the flexible base layer, wherein a titanium dioxide-polydopamine composite layer is arranged in a gap of the electrode inducing layer, and a platinum electrode layer is arranged on the titanium dioxide-polydopamine composite layer. The flexible electrode can be prepared by the method described in the first aspect of the present invention.

The polydopamine is chelated with platinum atoms at the interface between the titanium dioxide-polydopamine composite layer and the platinum electrode layer.

Material of the electrode inducing layer is an insulating material, specifically the residual material remaining after the reaction between the molding adhesive and the acid.

As described above, the intermediate conductive layer has a thickness of 10-30 nm. The titanium dioxide-polydopamine composite layer has a thickness of 80-500 nm. The platinum electrode layer has a thickness of 0.3-5 μm.

The flexible electrode herein further comprises a sealing layer covering a part of the electrode inducing layer that is not covered by the stimulation electrode sites and the electrode connection points of the platinum electrode layer.

In the flexible electrode provided in the second aspect of the present invention, the flexible base layer and the platinum electrode layer are connected through an intermediate conductive layer and an adhesive titanium dioxide-polydopamine composite layer. The titanium dioxide-polydopamine composite layer forms chemical bonds with the platinum electrode layer and the intermediate conductive layer through its various molecular bonds so as to improve the adhesion between them with the help of non-covalent bonds, thereby enhancing the bonding between the platinum electrode layer and the flexible base layer to a certain extent. The resulting patterned platinum electrode layer has a small electrical impedance, which improves its safety in biological applications.

The following experiments are performed to verify the function of nano-$TiO_2$ in the rapid formation of titanium dioxide-polydopamine composite layer and platinum electrode layer.

Two identical wafers of silicon (1 cm×1 cm in size) having a polyimide film on their surfaces are provided. The wafers are coated with a polydopamine precursor solution containing nano-$TiO_2$ and a polydopamine precursor solution without nano-$TiO_2$, respectively. The wafers are then placed under ultraviolet light having a wavelength of 365 nm to complete the deposition of the polydopamine film. The polydopamine (PDA) precursor solution containing nano-$TiO_2$ is prepared as follows: dissolving dopamine hydrochloride (3-hydroxytyramine hydrochloride) in a 10 mM Tris buffer solution, and adjusting pH to 8.5 to form a polydopamine (PDA) precursor solution having a final concentration of dopamine hydrochloride of 2 mg/mL; adding an aqueous dispersion of an appropriate amount of nano-$TiO_2$ (mass concentration 1.7 wt %) to 100 mL of the above dopamine precursor solution while stirring to obtain a mixed solution.

The results are shown in FIG. 1. FIG. 1 (a) shows the morphology of the film and the corresponding contact angle formed after being irradiating under ultraviolet light for 1 hour in the presence of nano-$TiO_2$. FIG. 1 (b) shows the morphology of the film and the corresponding contact angle formed after being irradiating under ultraviolet light for 6 hours in the absence of nano-$TiO_2$. It can be seen from FIG. 1 that the film formed after 1 hour of ultraviolet light irradiation in the presence of nano-$TiO_2$ is similar to the film formed after 6 hours of ultraviolet light irradiation in the absence of nano-$TiO_2$, because they have similar small contact angles, which indicates the formation of a hydrophilic polydopamine film. However, in the presence of nano-$TiO_2$, the formation of polydopamine film is greatly accelerated and shortened to 1 hour. The formation of a polydopamine film traditionally requires 24 hours. The present invention, by contrast, greatly improves the film formation efficiency. FIG. 1 (a) involves a $TiO_2$-PDA composite film, where nano-$TiO_2$ particles are uniformly distributed in the PDA film; FIG. 1 (b) involves a pure PDA film.

Figure 2:
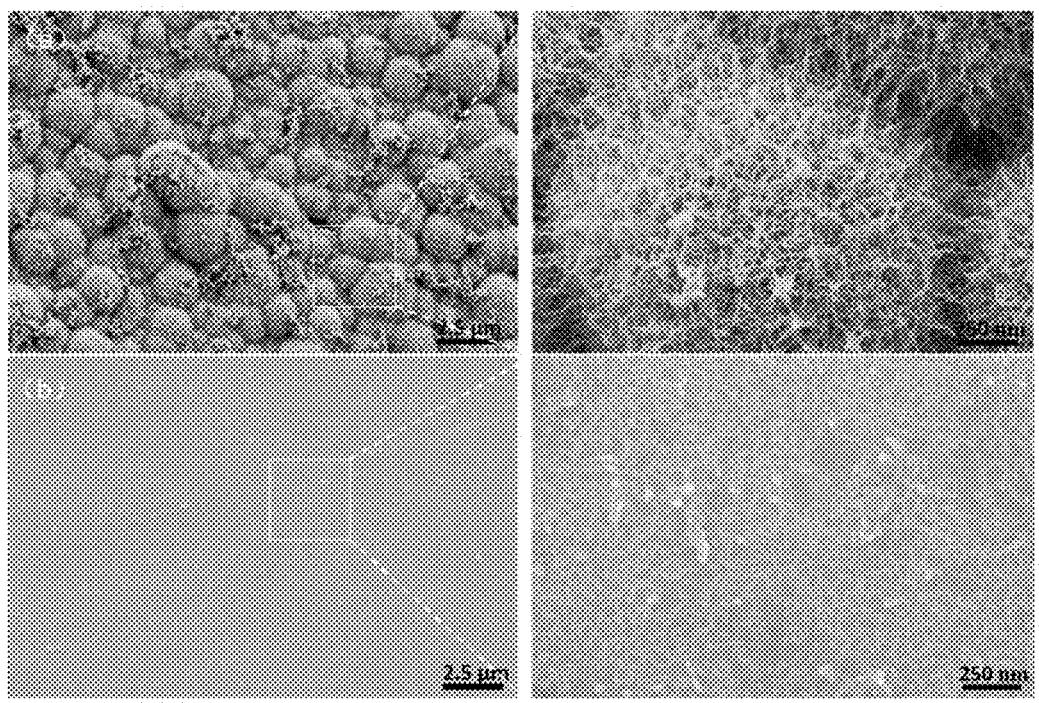
FIG. 2 shows the morphology of platinum ion deposited on the polydopamine film (a) in the presence of nano-$TiO_2$ and (b) in the absence of nano-$TiO_2$, and the picture on the right is an enlarged view of the white box in the picture on the left.

A platinum ion solution is prepared by mixing 2.5 mM aqueous solution of chloroplatinic acid and 5 mM aqueous solution of formic acid. The $TiO_2$-PDA composite film and PDA film are immersed into the above platinum ion solution, and treated with the same ultraviolet light for 6 hours to reduce platinum ions. The results are shown in FIG. 2. FIG. 2 (a) shows the morphology of the metal coating reduced by platinum ions on the surface of the $TiO_2$-PDA composite film and the magnified image; FIG. 2 (b) shows the morphology of the coating reduced by platinum ions on the surface of the PDA film and the magnified image.

It can be seen from FIG. 2 that in the absence of nano-$TiO_2$, even after 6 hours of ultraviolet light irradiation, no platinum metal layer is formed on the surface of the PDA film. In the presence of nano-$TiO_2$, under the irradiation of ultraviolet light for 6 hours, a regular platinum metal layer is formed on the surface of the $TiO_2$-PDA composite film. Compared with the requirement of more than 72 hours to deposit the platinum metal layer in the prior art, this shortens the period of the preparation of platinum metal layer by 11 times and thus greatly saves time.

Based on the result of the above experiments, the present invention will be explained with reference to an illustrative embodiment. Referring to FIG. 3 to FIG. 6, an embodiment of the present invention provides a method for preparing a flexible electrode, comprising the following steps.

(1). A wafer of silicon is provided as a carrier plate. First, the wafer is washed sequentially with acetone, absolute ethanol and deionized water. The wafer surface is coated with a solution of polyimide acid by spin coating at 500 rotations for 10 s and 2500 rotations for 40 s, resulting in a wet film. The film is baked at 100° C. for 3 minutes and then transferred to a vacuum dryer for high-temperature baking at 300° C. for 30 minutes such that the polyimide acid is cyclized to form a 5 μm thick polyimide (PI) film, i.e., PI flexible base layer 10.

(2). A 10 nm thick Au conductive layer 20 is formed on the 5 μm thick PI flexible base layer 10 as prepared at step (1) by a plasma evaporation method. The conductive layer can subsequently be used as an electrode position for DC electrophoresis electroplating.

Figure 3:
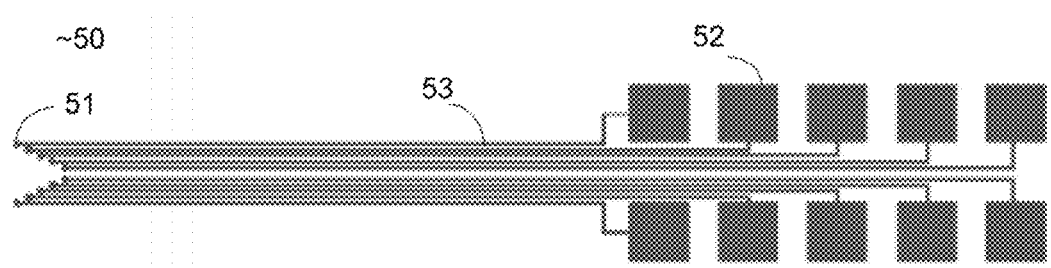
FIG. 3 shows a structural of a metal electrode layer of a flexible electrode according to an embodiment of the present invention.

(3). Preparation of an elastomeric template with an electrode pattern (3.1). Another wafer of silicon is provided as a hard substrate, on which a positive film with the electrode pattern is prepared by photolithography according to the well-designed pattern template of the flexible electrode (as shown in FIG. 3), which specifically comprises the following steps.

A layer of SU-8 photoresist is spin-coated on the cleaned silicon wafer. An exposure to 180 mJ/cm$^2$ ultraviolet light with a mask having a specific shape, and developing using SU-8 developer are performed after curing at 95° C. for 30 minutes. The part other than the mask is washed away to obtain the positive film of the electrode pattern.

A hot plate is used to harden the film at 120° C. for 15 minutes to volatilize the remaining solvent in the photoresist such that the positive film adheres to the surface of the wafer more firmly for later use.

Figure 4:
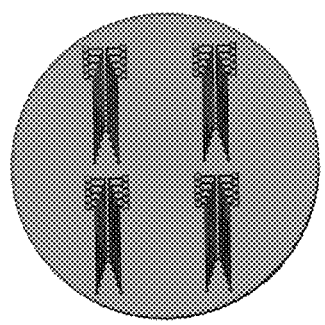
FIG. 4 shows the structure of a PDMS elastomeric template with an electrode structure according to an embodiment of the present invention.
Figure 5:
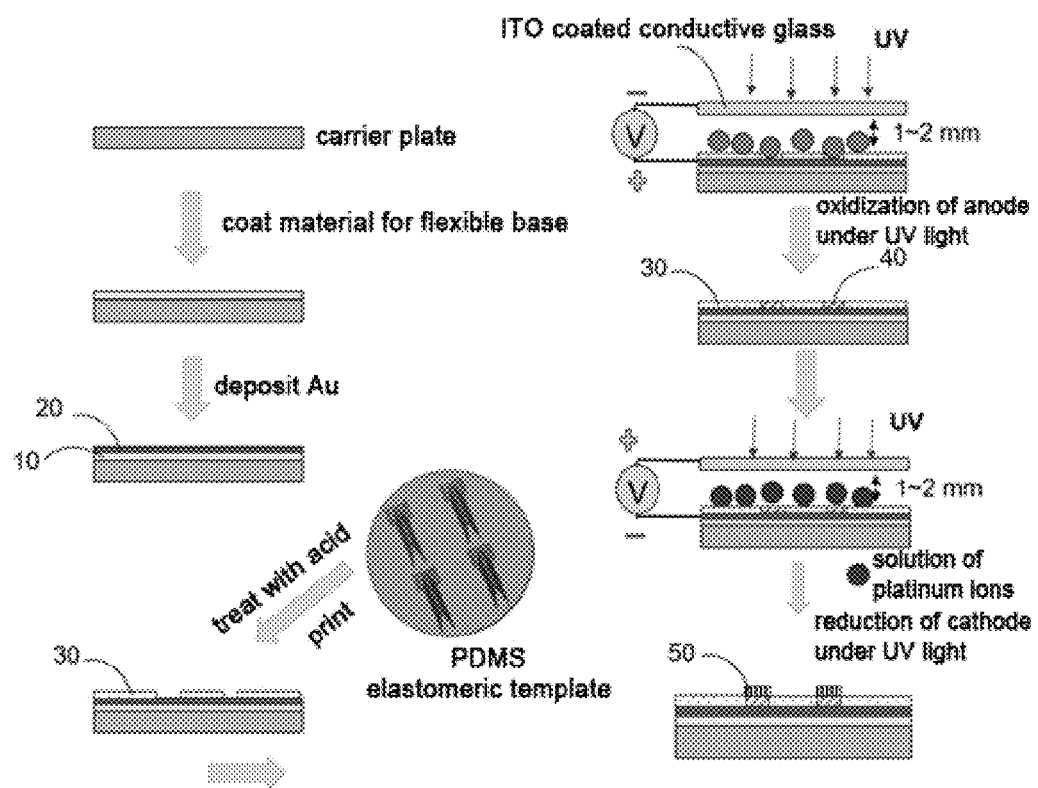
FIG. 5 shows a flow chart of preparation of a flexible electrode according to an embodiment of the present invention.

(3.2). Casting a molding adhesive onto the above positive film, and then debubbling, curing and removing the film, an elastomeric template with the electrode pattern is obtained; the elastomeric template has a pattern complementary to the positive film. The molding adhesive used herein can be, for example, polydimethylsiloxane (PDMS). The PDMS used herein for casting may comprise glue A and glue B in a volume ratio of 1:10. After the bubbles are removed by the deaerator, the curing process is carried out (for example, in an oven at 80° C. for 3 hours). After curing, the electrode pattern in the positive film can be reliably transferred and printed onto the molding adhesive. Then the cured molding adhesive layer is removed from the wafer to obtain a PDMS elastomeric template with electrode structure (as shown in FIG. 4).

(4). A mixed acid solution of hydrofluoric acid (HF) and nitric acid in a volume ratio of 3:1 is prepared, and the PDMS elastomeric template prepared at step (3) is dipped on the mixed acid solution. The electrode pattern of the PDMS electrode template had been dipped with the mixed acid solution is transferred and printed onto the surface of the Au conductive layer 20 of step (2) by microcontact printing (the surface of the Au conductive layer 20 preferably maintains wet before transferring and printing) such that an electrode inducing layer 30 is formed on the Au conductive layer 20 (as shown in FIG. 3). The material of the electrode inducing layer 30 is the residual material remaining after the treatment on PDMS with acid. A pressure of 1.8 N is applied during the microcontact printing. The transferred electrode inducing layer 30 has a shape complementary to the electrode pattern. That is, the groove of the electrode inducing layer 30 corresponds to the electrode to be formed.

After the step of transferring, it is washed with deionized water and dried with nitrogen for later use.

(5). The TiO$_2$-PDA composite layer 40 is deposited by direct current electrophoresis under light:

(5.1). Preparation of a mixture of nano-TiO$_2$ and polydopamine (PDA) precursor solution: dissolving dopamine hydrochloride (3-hydroxytyramine hydrochloride) in 10 mM Tris buffer solution, adjusting pH to 8.5 to form the polydopamine precursor solution having a final concentration of dopamine hydrochloride of 2 mg/mL; adding an aqueous dispersion of an appropriate amount of nano-TiO$_2$ (mass concentration 1.7 wt %) to 100 mL of the above dopamine precursor solution while stirring to obtain the mixed solution.

(5.2). The wafer stacked with PI flexible base layer 10, Au conductive layer 20 and electrode inducing layer 30 of step (4) is provided. The mixed solution as prepared is added to a part of Au conductive layer 20 that is not covered by electrode inducing layer 30. Using the glass with ITO coating as the cathode and the Au conductive layer 20 as the anode, and disposing the ITO coating and the Au conductive layer 20 opposite to each other. The distance between cathode and anode is within 1-2 mm, and a DC voltage of 5V is applied between cathode and anode; TiO$_2$-PDA composite layer 40 is formed in the gap of the electrode inducing layer 30 by electroplating and oxidizing the anode under ultraviolet light, followed by washing with ultrapure water and drying for later use.

Ultraviolet light is applied to the ITO coated glass on the side that has no ITO coating such that the ultraviolet light reaches the mixed solution. The ultraviolet light has an energy density of 2 mW/cm$^2$. The ultraviolet light is applied for 5 minutes; a DC voltage between the anode and the cathode is applied for 5 minutes, and the formed TiO$_2$-PDA composite layer 40 has a thickness of 100 nm.

(6). The platinum electrode layer 50 is deposited by direct current electrophoresis under light:

80 mL, 2.5 mM chloroplatinic acid aqueous solution and formic acid are mixed, and deionized water is added to obtain 100 mL of the mixed solution, resulting in the platinum ion solution required for depositing the platinum electrode layer.

The platinum ion solution is added to the surfaces of the TiO$_2$-PDA composite layer 40 and the electrode inducing layer 30. At this time, the above-mentioned ITO coated glass is used as the anode, the Au conductive layer 20 is used as the cathode, and the ITO coating of the glass is arranged to face the Au conductive layer 20. The distance between the cathode and the anode is within 1-2 mm, and a DC voltage of 5V is applied between the cathode and anode; platinum electrode layer 50 is formed on the TiO$_2$-PDA composite layer 40 by reducing the cathode under ultraviolet light, followed by washing with ultrapure water and drying for later use.

Ultraviolet light is applied to the ITO coated glass on the side that has no ITO coating such that the ultraviolet light reaches the platinum ion solution. The ultraviolet light has an energy density of 2 mW/cm$^2$. The ultraviolet light is applied for 1 hour; a DC voltage between the anode and the cathode is applied for 1 hour, and the formed platinum electrode layer 50 has a thickness of 0.5 µm.

(7). Preparation of the sealing layer 60 of the flexible electrode.

(b1). A sealing film 60' is provided on the platinum electrode layer 50, and the sealing film 60' also covers a part of the electrode inducing layer 30 that is not covered by the platinum electrode layer 50. The material of the sealing film 60' can be PI, and the preparation is as follows.

First, the carrier plate with the platinum electrode layer 50 is heated at 120° C. for 5 minutes to remove water vapor, and then it is coated with a polyimide acid solution by a homogenizer to form a 5 µm thick wet film; after being baked at 100° C. for 3 minutes, the sample being softened for 3 minutes is placed in the oven for quickly heating from room temperature (about 25° C.) to 40° C., and then to 300° C. at a rate of 3° C./min. After being baking at a high temperature for 30 minutes, the polyimide acid cyclizes to generate PI, and it is naturally cooled to room temperature.

(b2). the sacrificial material (specifically AZ4620 positive photoresist) is coated on the PI sealing film 60' at 300 revolutions for 15 seconds and 3000 revolutions for 30 seconds to create a sacrificial layer having a thickness of about 3 µm; the sacrificial layer is exposed to ultraviolet light (having a density of 40 mJ/cm$^2$), and then is subjected to a post-baking treatment at 120° C. It is developed with AZ300 developer after being cooled to room temperature. A patterned sacrificial layer 70 is formed. The patterned sacrificial layer 70 does not cover stimulation electrode sites 51 and electrode connection points 52 of platinum electrode layer 50 (see FIG. 3).

(b3). Using the patterned sacrificial layer 70 as a mask, perform plasma (RIE) etching on the PI sealing film 60' to expose stimulation electrode sites 51 and electrode connection points 52 of platinum electrode layer 50 that is covered, leaving other parts such as wires unexposed. The sealing layer 60 is thereby formed. The etching is performed under the following conditions: oxygen flow rate: 40 sccm, chamber pressure: 20-14 pa, power: 150 W, time: 10 min, repeat 4 times.

(b4). Immersing the RIE-etched sample in acetone to completely dissolve the sacrificial material (AZ4620 positive photoresist) remaining in acetone, followed by washing the surface with deionized water and drying with nitrogen to obtain a flexible electrode with a sealing layer 60.

Figure 6:
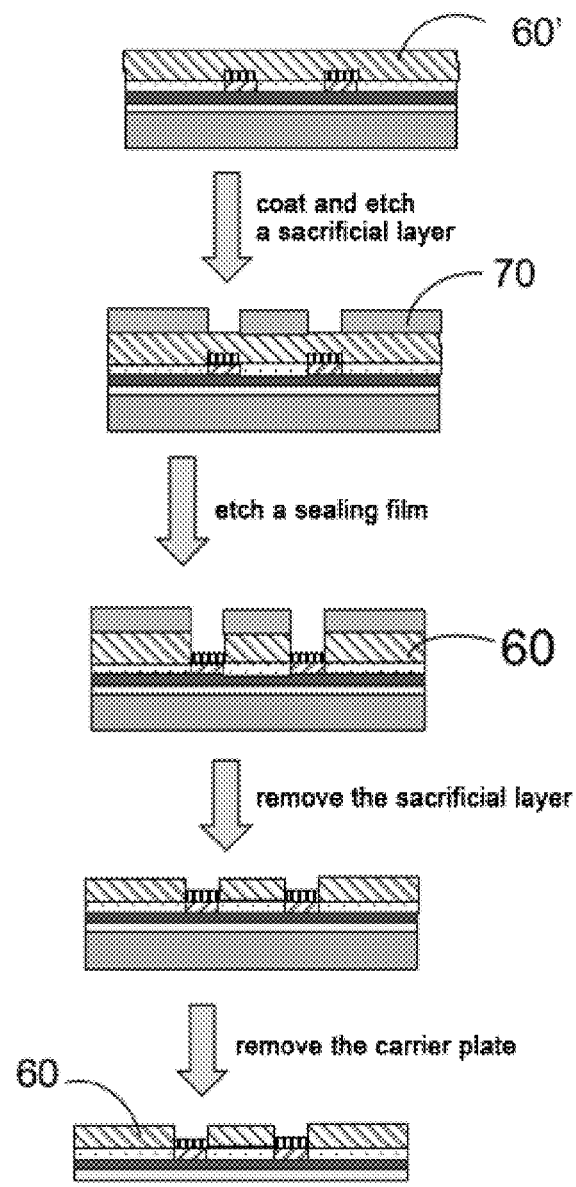
FIG. 6 shows a process of sealing the flexible electrode in FIG. 3 according to an embodiment of the present invention.

(8). Remove the carrier wafer connected to the PI flexible base layer 10 to complete the production of the flexible electrode. The resulting flexible electrode product is shown in FIG. 6.

FIG. 3 shows a structural design of the platinum electrode layer 50 of the flexible electrode according to one embodiment of the present invention. The platinum electrode layer 50 comprises 10 stimulation electrode sites 51 and 10 electrode connection points 52 arranged oppositely, and each stimulation electrode site 51 connects to each electrode connection point 52 via a wire 53. In FIG. 3, the diameter of the stimulation electrode site 51 is 200 μm, the width of the wire 53 is 35 μm, and the electrode connection point 52 is a 1*1 mm square, which can be connected to a PCB board with a chip or connected to other devices for testing.

Figure 7:
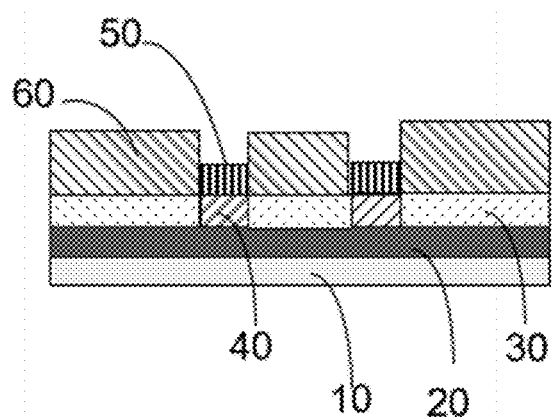
FIG. 7 shows the structure of the flexible electrode obtained after the process in FIG. 6.

FIG. 7 shows the structure of the sealed flexible electrode according to one embodiment of the present invention. As shown in FIG. 3, the flexible electrode comprises a flexible base layer 10 and an intermediate conductive layer 20 and an electrode inducing layer 30 sequentially arranged on a surface of the flexible base layer 10. A titanium dioxide-polydopamine composite layer 40 is arranged in a gap of the electrode inducing layer 30, and a platinum electrode layer 50 is arranged on the titanium dioxide-polydopamine composite layer 40.

The flexible electrode further comprises a sealing layer 60 covering a part of the electrode inducing layer 30 that is not covered by the stimulation electrode sites 51 and the electrode connection points 52 of the platinum electrode layer 50. In other words, both electrode inducing layer 30 and platinum electrode layer 50 are arranged in the accommodating space of the sealing layer 60, but stimulation electrode sites 51 and electrode connection points 52 of platinum electrode layer 50 are exposed from the sealing layer, leaving the wires of the electrode layer 50 unexposed.

Figure 8:
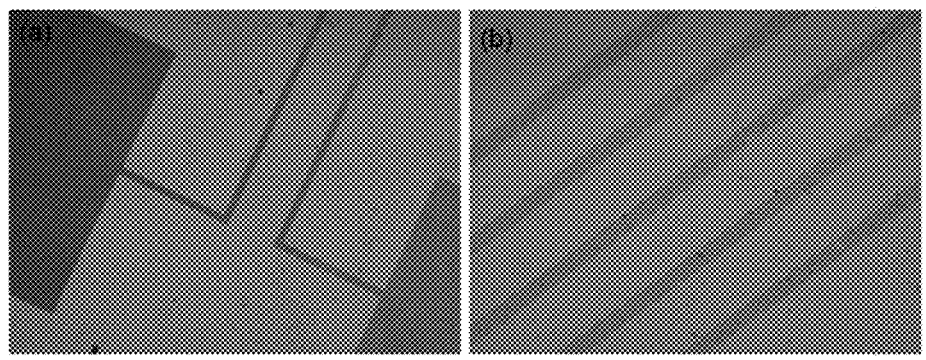
FIG. 8 shows the morphology of a titanium dioxide-polydopamine composite layer formed according to an embodiment of the present invention, where (a) and (b) are observation results of different areas.
Figure 9:
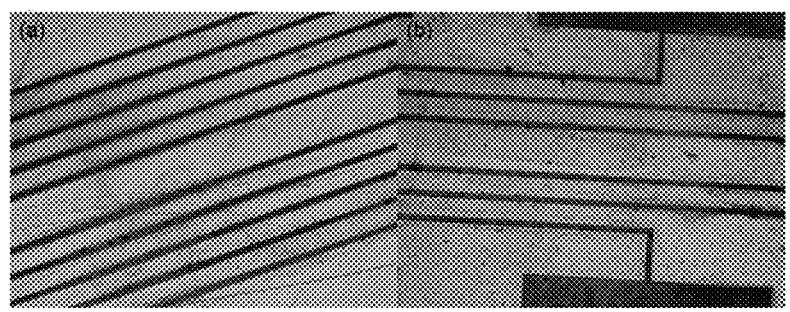
FIG. 9 shows the morphology of a platinum electrode layer formed according to an embodiment of the present invention, where (a) and (b) are observation results of different areas.

FIG. 8 shows morphology of a TiO$_2$-PDA composite layer formed by DC electrophoresis under light according to one embodiment of the present invention. FIG. 9 shows morphology of a platinum electrode layer formed by DC electrophoresis under light according to one embodiment of the present invention. It can be seen from FIG. 8 that a deep yellow TiO$_2$-PDA composite layer can be quickly formed through the anode by using DC electrophoresis and ultraviolet light in the presence of nano-TiO$_2$. It can be seen from FIG. 9 that a black platinum electrode layer can be quickly formed on the TiO$_2$-PDA composite layer by using DC electrophoresis and ultraviolet light. Moreover, both TiO$_2$-PDA composite layer and platinum electrode layer form a coating in a predetermined groove, and show a clear edge. The results indicate that the method for preparing flexible electrode according to the present invention permits to quickly and directly prepare a TiO$_2$-PDA composite layer and a platinum electrode layer with a regular structure.

The foregoing descriptions are merely specific embodiments of the present invention, but are not intended to limit the protection scope of the present invention. Any variation or replacement readily figured out by a person skilled in the art within the technical scope disclosed in the present invention shall fall within the protection scope of the present invention. Therefore, the protection scope of the present invention shall be subject to the protection scope of the claims.

What is claimed is:

1. A method for preparing a flexible electrode, comprising:
    providing a carrier plate, and sequentially forming a flexible base layer and an intermediate conductive layer on a side of the carrier plate;
    preparing an elastomeric template with an electrode pattern, and treating the elastomeric template with an acid, followed by transferring and printing the electrode pattern of the elastomeric template onto a surface of the intermediate conductive layer by microcontact printing such that an electrode inducing layer complementary to the electrode pattern is formed on the intermediate conductive layer;
    adding a mixture of nano titanium dioxide and a solution of polydopamine precursor onto the intermediate conductive layer that is not covered by the electrode inducing layer, using a glass with a transparent conductive layer as a cathode, and the intermediate conductive layer as an anode, disposing the transparent conductive layer and the intermediate conductive layer opposite to each other, forming a titanium dioxide-polydopamine composite layer in a gap of the electrode inducing layer by electroplating and oxidizing the anode under ultraviolet light;
    adding a solution of platinum ion onto surfaces of the titanium dioxide-polydopamine composite layer and the electrode inducing layer, using a glass with a transparent conductive layer as an anode, and the intermediate conductive layer as a cathode, disposing the transparent conductive layer facing to the intermediate conductive layer, forming a platinum electrode layer on the titanium dioxide-polydopamine composite layer by reducing the cathode under ultraviolet light;
    removing the carrier plate to obtain the flexible electrode.

2. The method for preparing a flexible electrode of claim 1, wherein the elastomeric template with an electrode pattern is prepared by steps of
    applying a photoresist on a hard substrate by spin coating, and performing exposure with a mask having a specific shape and developing to obtain a positive film with the electrode pattern; and
    casting a molding adhesive onto the positive film, which is removed after curing to obtain the elastomeric template with the electrode pattern.

3. The method for preparing a flexible electrode of claim 1, wherein a pressure of 1.0-2.0 N is applied during the microcontact printing.

4. The method for preparing a flexible electrode of claim 1, wherein the acid comprises at least one of hydrofluoric acid, nitric acid and hydrochloric acid.

5. The method for preparing a flexible electrode of claim 1, wherein the solution of polydopamine precursor is a solution of dopamine hydrochloride in Tris, the solution having a pH of 6-9 and a concentration of dopamine hydrochloride of 2-5 mg/mL, and wherein a concentration of nano-titanium dioxide in the mixture is in a range of 0.05-0.25 mg/mL.

6. The method for preparing a flexible electrode of claim 1, wherein a DC voltage of 1-5V is applied between the cathode and the anode in the processes of oxidizing the anode and reducing the cathode.

7. The method for preparing a flexible electrode of claim 6, wherein a distance between the cathode and the anode is in a range of 1-5 mm in the processes of oxidizing the anode and reducing the cathode.

8. The method for preparing a flexible electrode of claim 1, wherein the ultraviolet light has an energy density of 0.7-5 mW/cm$^2$ in the processes of oxidizing the anode and reducing the cathode.

9. The method for preparing a flexible electrode of claim 7, wherein in the process of forming the titanium dioxide-polydopamine composite layer, the ultraviolet light is applied for 3-15 minutes, and the voltage is applied between the cathode and the anode for 3-15 minutes.

10. The method for preparing a flexible electrode of claim 7, wherein in the process of forming the platinum electrode layer, the ultraviolet light is applied for 20-120 minutes, and the voltage is applied between the cathode and the anode for 20-120 minutes.

11. The method for preparing a flexible electrode of claim 7, wherein the titanium dioxide-polydopamine composite layer has a thickness of 80-500 nm.

\* \* \* \* \*